United States Patent [19]

Papadakis et al.

[11] Patent Number: 5,091,181

[45] Date of Patent: Feb. 25, 1992

[54] ASPHODELUS COMPOSITION FOR INCREASING WHITE BLOOD CELL COUNT

[76] Inventors: Stavros Papadakis, W. Berwyn, Chicago, Ill. 60659; Konstantinos Papadakis, 9432 Bay Colony, Des Plaines, Ill. 60016

[21] Appl. No.: 555,583

[22] Filed: Jul. 19, 1990

[51] Int. Cl.$^5$ ...................... A61K 35/78; A61K 39/00
[52] U.S. Cl. .................... 424/195.1; 424/88; 514/783; 514/908
[58] Field of Search ............... 424/195.1, 88; 514/908, 514/783

[56] References Cited

U.S. PATENT DOCUMENTS

| | | | |
|---|---|---|---|
| 40,189 | 10/1863 | Scott | 424/195.1 |
| 43,118 | 6/1864 | Knoebel | 424/195.1 |
| 65,302 | 5/1867 | Thurmon | 424/195.1 |
| 117,338 | 7/1871 | Simmons | 424/195.1 |
| 132,233 | 10/1872 | Barnes | 424/195.1 |
| 135,083 | 2/1873 | Geomen | 424/195.1 |
| 4,518,591 | 5/1985 | Iida | 424/195.1 |
| 4,716,120 | 12/1987 | Tsay | 436/513 |

OTHER PUBLICATIONS

King, J., American Dispensatory, 8th Ed., Cincinnati, 1870, pp. 965-967.
Steinmetz, E. F., Codex Vegetabilis, 1957, Amsterdam, #161.
Bailey, Standard Cyclopedia of Horticulture, Macmillan Co., New York, 1935.
Chittenden, Dictionary of Gardening, Clarendon Press, Oxford, 1956.
Fell et al., J. Pharm. Pharmac., 20: 646-649 (1968).
Hommouda et al., Chemical and Pharmacological Studies of *Asphodelus Microcarpus*, PLMEAA, 22(2), 109-212 (1972).
Hammouda et al., Die Pharmazie, Pharmazie, 29, H. 9 (1974).
Madaan et al., Indian Journal of Biochemistry & Biophysics, vol. 10, Mar. 1973, pp. 55-58.
Scarborough, Clinics in Plastic Surgery, vol. 10/No. 4, Oct., 1983.
R. M. T. Dahlgren et al., The Families of Monocotyledons-Structure, Evolution and Taxonomy, Springer-Verlag, New York, (1985).
AIDS and the Election, Scientific American, vol. 259, No. 4, p. 14 (1988).
AIDS: an Unknown Distance Still to Go, Scientific American, vol. 259, No. 4, p. 152 (1988).
AIDS IN, Scientific American, vol. 259, No. 4, p. 40 (1988).
The Molecular Biology of the AIDS Virus, Scientific American, vol. 259, No. 4, p. 52 (1988).
The Origins of the AIDS Virus, Scientific American, vol. 259, No. 4, p. 64 (1988).
HIV Infection: the Clinical Picture, Scientific American, vol. 259, No. 4, p. 90 (1988).
HIV Infection: the Cellular Picture, Scientific American, vol. 259, No. 4, p. 100 (1988).
AIDS Therapies, Scientific American, vol. 259, No. 4, p. 110 (1988).
AIDS Vaccines, Scientific American, vol. 259, No. 4, p. 120 (1988).
The Epidemiology of AIDS in the U.S., Scienific American, vol. 259, No. 4, p. 72 (1988).
The Social Dimension of AIDS, Scientific American, vol. 259, No. 4, p. 128 (1988).
The International Epidemiology of AIDS, Scientific American, vol. 259, No. 4, p. 82 (1988).

*Primary Examiner*—Ronald W. Griffin
*Assistant Examiner*—Ralph Gitomer
*Attorney, Agent, or Firm*—Laff, Whitesel, Conte & Saret

[57] ABSTRACT

A composition and method for treating white blood cell deficiency in human beings or animals that includes, as an active pharmaceutical agent, an effective amount of an edible herb extract wherein the edible herb is from the genus Asphodelus, with the active agent being admixed with a pharmaceutically acceptable carrier.

22 Claims, No Drawings

ASPHODELUS COMPOSITION FOR INCREASING WHITE BLOOD CELL COUNT

FIELD OF THE INVENTION

This invention relates to a composition and method that increases the number of white blood cells in human beings. More particularly, this invention relates to a composition and method that increases the number of white blood cells, and lymphocytes, and thus prevents complete immune system dysfunction.

BACKGROUND OF THE INVENTION

To date, there are several widespread diseases that are often fatal and which generally involve a certain type of white blood cell that is responsible for orchestrating the immune system of the body. Among such diseases, included are two highly malignant cancers known as adult T-cell leukemia (ATL) and acquired immuno-deficiency syndrome (AIDS). These diseases not only infect the same type of white blood cell but further share another crucial feature in that they are all caused by a class of infectious agents known as retroviruses.

Retroviruses are viruses that cannot replicate without controlling and exploiting the biosynthetic apparatus of a cell for different purposes. Retroviruses consist of the genetic material of RNA and are capable of reversing the ordinary flow of genetic information—from DNA to RNA to proteins. Additionally, retroviruses carry an enzyme called reverse transcriptase, which uses the viral RNA as a template for making DNA. The viral DNA integrates itself into the genome of the host wherein it remains latent until it is activated to make new virus particles. Much attention is being paid to the human immunodeficiency virus (HIV) retrovirus which causes AIDS due to its rapid transmission, progressive derangement of immune function and high fatality rate.

It appears that the HIV retrovirus enter a cell by binding to a molecule known as the CD4 antigen. The CD4 antigen is found primarily on specific set of white blood cells of the immune system called T4 lymphocytes or helper T cells. Accordingly, HIV infection is characterized by the loss of these T-lymphocyte cells, which causes a deterioration of the immune system.

The T-lymphocyte cell is crucial to the immune system in that, among other functions, it recognizes foreign antigens, or markers, on infected cells and helps to activate another set of lymphocyte white blood cells which multiply and produce antibodies that bind to infected cells. The T-lymphocyte cell further is capable of completely eliminating infected cells. Thus, the loss of T-lymphocyte cells not only seriously impairs the body's ability to fight most invaders, but also has a severe impact on the defenses against viruses, fungi, parasites and certain bacteria.

To date, there is no known cure for AIDS. There are presently various experimental drugs on the market including an antiviral substance known as azidothymidine (AZT) which has been shown to prolong the lives of certain AIDS patients. While AZT and other drugs have shown to be beneficial, they do not benefit all patients and accordingly, new solutions are needed. Moreover, the present drugs are for the most part extremely expensive and often difficult to obtain.

In the case of AIDS and some forms of hepatitis and leukemia, it is the secondary infections which are the actual cause of death. There is, therefore, a need for a means of treating such immune deficiency-causing diseases which boosts the suppressed lymphocyte levels and provides a defense against life-threatening secondary infections.

SUMMARY OF THE INVENTION

Accordingly, an object of the present invention is to provide a composition and method that increases the number of white blood cells.

Another object of the present invention is to provide a composition and method that increases the number of white blood cells and increase the number of lymphocytes.

A further object of the present invention is to provide a composition and method that prevents complete immune system dysfunction.

A further object of the present invention is to provide a composition and method that is easily administered to the patient and which is relatively inexpensive.

A further object of the present invention is to provide a composition and method that is simple to manufacture.

The objectives and advantages of the present invention are achieved by providing a composition and method that involves preparing a plant extract and/or plant solution for internal consumption, such preparation having a medicinal application in that the number of white blood cells and lymphocytes are returned to normal levels and/or higher.

The foregoing plant extract and/or solution is made by a simple process involving an edible herb, specifically a Mediterranean and West Asiatic plant known as Asphodelus tenuifolius. The genus Asphodelus describes a hardy, herbaceous stemless plant having white, lily-like flowers in long racemes, fleshy fascicled roots and firm, linear, radical, tufted leaves. It generally grows as a common weed in the above-cited locations.

More specifically, the composition derives form one species of asphodel, a purple-flowering variant of *Asphodelus tenuifolius* which occurs in Greece and Turkey. This identification is based on R.M.T. Dahlgren, et al's "The Families of Monocotyledons—Structure, Evolution and Taxonomy", Springer-Verlag, New York (1985).

Minor discrepancies of plant classification are often found between different botanists' works. Therefore, *A. tenuifolius* has been described as "identical" to *A. microcarpus* and *A. aestivus* by some classifiers of the plant (see Bailey, Standard Cyclopedia of Horticulture, Macmillan Co., New York, 1935), and alternatively as "allied to" *A. fistulosis* by others (see Chittenden, Dictionary of Gardening, Clarendon Press, Oxford, 1956). These species are closely related; accordingly, it is expected that asphodel species other than *A. tenuifolius* will be identified which, when prepared using the method of the present invention, will yield an equally therapeutic composition.

An identification of each of the components of the aqueous extract has not been carried out, but it may be anticipated that the extract will be found to contain a wide variety of phytochemicals. Analyses of the constituents of *A. microcarpous* and *A. fistulosis* have shown that these related species both contain numerous saccharides, fatty acids, sterols, and plant alkaloids; investigation of *A. tenuifolius* is likely to reveal similar components. (See Fell et al., *T. Pharm. Pharmac.* 20:646–649 (1968).)

It is known that the genus Asphodelus has a wide variety of applications. For example, *Asphodelus microcarpus* has been used as a remedy for paralysis by applying same locally on the exterior of the human body. Other studies reveal that the seeds of the species *Asphodelus microcarpus* and *Asphodelus fistulosus* contain fixed oil, carbohydrates (free sugars and mucilage), phenolic substances and alkaloids. Moreover, other experimentation has been concerned with the quantitative determination and seasonal variation of the anthraquinones of *Asphodelus microcarpus* and *Asphodelus fistulosus*. Still further studies have shown that *Asphodelus tenuifolius* and fistulosus may be used as a human food source due to their high protein content.

In contrast to the prior uses of the various species of Asphodelus, including the species of tenuifolius, the present inventive composition and use thereof is concerned with a pharmaceutical use involving the consumption of a solution that eventually increases the number of white blood cells and lymphocytes. Thus, the elevation of lymphocyte levels by an aqueous extract of seed capsules, roots, and stems is unanticipated in the prior art, however, and is a new and unexpectedly valuable use of the *A. tenuifolius* plant.

The preferred process for making the above-mentioned *Asphodelus tenuifolius* extract and/or solution generally comprises the steps of: (1) washing the entire Asphodelus tenuifolius plant collected in its dry state; (2) boiling a specific amount of the dried plant in water; (3) removing the boiled plant and resulting residue from the solution; and (4) storing said solution containing the plant extraction until administration to patient is effectuated. The extract is preferably stored in a dark, cool environment having a temperature between 4°-8° C.

DETAILED DESCRIPTION OF THE INVENTION

The present invention contemplates preparing an extract and/or solution that involves washing approximately three to four *Asphodelus tenuifolius* plants collected in their dry state. The entire plant is used in this procedure, including the whole woody stem, the root system, the loculicidal capsules and the seeds. Each loculicidal capsule contains from five to six seeds with the number of seeds on one plant being within the range of 300-500 depending on the plant's growth. Approximately 50 grams, which corresponds to three to four plants, of *Asphodelus tenuifolius* are placed into approximately two liters of water. The water is then boiled for about twenty minutes during which time the extraction process occurs. Approximately 600 milliliters of the water evaporates during boiling. A residue will form during the extraction process. The residue is removed along with the boiled plant(s) so that the remaining solution contains only the *Asphodelus tenuifolius* extract mixed in with the water. This above-described solution is ingested by patients and will be described in greater detail hereinafter.

The following Examples illustrate the inventive method and use.

EXAMPLE 1

Toxicity of the inventive composition was tested for by behavioral and physiological examination of laboratory animals given the composition. These studies were carried out using rats and rabbits. The test animals' water supply was replaced for a two week period with a diluted form of the *Asphodelus tenuifolius* extraction. Thereafter, pure water was again supplied.

No irregularities of behavior or water consumption were noted to confirm the non-toxicity of the solution and the lack of side effects. Moreover, two days after their return to pure water, a limited gross necropsy was performed on two of the animals used in the experiment to examine any change in the internal organs. No apparent changes were observed.

The animals were examined again after a two month period and the effect was the same as for the two-week period.

EXAMPLE 2

A second toxicity experiment that involved varying the concentration of the *Asphodelus tenuifolius* and administering daily doses of approximately 1 ml. The doses were administered by oral gavage. The concentrations were calculated by the ratio between *Asphodelus tenuifolius* weight in grams and solvent volume. Generally, the mice were administered 1 ml doses of Asphodelus tenuifolius extract at concentrations of 25%, 50% and 100%. Again, no adverse reactions were noted. The test animals appeared normal irrespective of dose, supporting a conclusion of non-toxicity.

EXAMPLE 3

The immunomodulatory properties of *Asphodelus tenuifolius* were studied using CD-1 female mice injected with an LD65-90 of Herpes simplex type 2 virus (HSV-2)(a dosage of virus causing an expected mortality of 65% to 90% of the test animals). Four groups of animals were used, each receiving by oral gavage a daily 0.5 ml dose of the composition at various concentrations of 0%, 25%, 50%, and 100%, respectively. The composition (or the aqueous control) was administered for five days, with the viral challenge occurring during the third day of the study.

After intraperitoneal injection of the virus, the test animals were monitored for mortality for a period of 21 days. The following results were obtained:

TABLE 1

| Composition Strength | Mean Survival Time | Dead/Total | Mortality |
|---|---|---|---|
| 100% | 17.4 days | 7/20 | 35% |
| 50 | 16.3 | 9/20 | 45 |
| 25 | 14.7 | 11/20 | 55 |
| 0 | 15.0 | 9/19 | 47 |

As shown above, the survival times and percentages were found to be noticeably improved among test animals given increasingly stronger doses of the composition. These results support the conclusion that the inventive composition, even when given only temporarily, may have the potential for a therapeutic effect. It should be noted that the composition did not destroy the virus.

The above study also included one group of test animals at each concentration of composition which was not exposed to viral challenge. These toxicity controls were found to remain normal in all respects, confirming the earlier conclusions regarding toxicity of the composition.

EXAMPLE 4

Several male human volunteers suffering from a variety of diseases involving a compromised immune system, were treated by oral administration of the composition. Doses of 150 ml were given once or twice daily while levels of white blood cells (WBC) were monitored. The number of days until remission or initial recovery was also noted.

The age, disease and number of *Asphodelus tenuifolius* extract doses given to each male is shown in Table 2. Thus, as Table 2 indicates, the infected males were given from 10 to 16 doses of *Asphodelus tenuifolius* over a period of 7 to 10 days. The results of the above treatment, visualized in Table 2, show that it took the infected males from between 7 to 10 days to achieve a normal white blood cell count and corresponding lymphocyte count.

TABLE 2

| Volunteers | Disease diagnosed | Number of doses | Number of days |
|---|---|---|---|
| I Male, 14 year old | infectious hepatitis Spherocytic anemia | 14 | 7 |
| II Male, 20's | A.I.D.S. (advanced) acute encephalitis | 10 | 8 |
| III Male, 50's | Severe myelogenic leukemia | 12 | 9 |
| IV Male, 50's | leukemia | 12 | 10 |
| V Male, 50's | leukemia | 13 | 10 |
| VI Male, 23 years | A.I.D.S. virus carrier early stage | 16 | 10 |
| VII Male, 40's | Low WBC/lymphocyte count (suspected AIDS case | 15 | 10 |

EXAMPLE 5

*Asphodelus tenuifolius* extract was administered to a male subject who was suffering from a liver deficiency and was also anemic. Specifically, the patient had to maintain his white blood cell count. The *Asphodelus tenuifolius* extract was given to the patient. His blood was tested by different practitioners and at different medical facilities.

The patient's blood was drawn and analyzed prior to his ingestion of the *Asphodelus tenuifolius* extract. Such analysis revealed the following blood breakdown:
5,500,000 red blood cells
16.2 grams hemoglobin
50% hematocrit
200,000 blood platelets
The patient's blood analysis further included 4500 white blood cells which had 1665 lymphocytes.

Subsequent to the above blood analysis, the patient was given two doses of *Asphodelus tenuifolius* extract with each dose approximately 8 hours apart. Two doses were similarly administered for the next three days. Each dose consisted of approximately 150 to 170 ml of extract solution.

The patients blood was drawn and analyzed on the fourth day. The results of the blood analysis were as follows:
5,500,000 red blood cells
16.1 grams hemoglobin
50% hematocrit
180,000 blood platelets.
The results showed that there was no remarkable change in the number of red blood cells since the initial analysis. The white blood cells, however, showed a dramatic change. The results were 5000 white blood cells which had 2250 lymphocytes. Thus, the results showed that after only four days of ingestion of *Asphodelus tenuifolius*, the subject's white blood cell count had increased from 4500 to 5000 and that the number of lymphocytes had increased from 1665 to 2250.

After the fourth day blood analysis, the subject continued receiving two doses per day, at similar intervals, from the fifth to the ninth day, until blood was again drawn and analyzed on the ninth day. The ninth day results were as follows:
5,100,000 red blood cells
15.6 grams hemoglobin
47% hematocrit
unknown - blood platelets
7300 white blood cells which had 2920 lymphocytes.
Again, the results showed that the white blood cell count had increased from 5000 to 7300 and the lymphocyte count from 2250 to 2920 from the fourth day to the ninth day.

The patient did not receive any doses of the *Asphodelus tenuifolius* extract from the 10th day through the 14th day. Also, during this same time period, the patient went on a short excursion and over-exerted himself. The absence of the *Asphodelus tenuifolius* extraction, coupled with a period of excess activity, caused the patient's white blood cell and lymphocyte count to decrease. A blood drawing and analysis on the 15th day showed the following:
5,500,000 red blood cells
16.9 grams hemoglobin
50% hematocrit
180,000 blood platelets
3,500 white blood cells which had 1295 lymphocytes.
Due to the decrease in the patient's white blood cell and lymphocyte count, two doses were again given to the patient on the 16th and 17th day and on the 17th day, the patient's blood was drawn and analyzed, revealing:
5,160,000 red blood cells
16.0 grams hemoglobin
48% hematocrit
300,000 blood platelets
7000 white blood cells which had 3220 lymphocytes.
Thus, the results reveal that after the patient was again given the doses of *Asphodelus tenuifolius*, the white blood cell count increased from 3500 to 7000 and the lymphocytes from 1295 to 3220 during this period.

The patient continued to take two doses per day from the 18th to the 27th day. On the 27th day blood was drawn and analyzed, showing:
5,300,000 red blood cells
16.2 grams hemoglobin
50% hematocrit
300,000 blood platelets
6500 white blood cells which had 2665 lymphocytes.
The results showed a slight decrease in white blood cell and lymphocyte count. This may have been attributed to an increase in activity by the patient or possibly normal cell count fluctuation.

The patient continued taking doses of *Asphodelus tenuifolius* through the 37th day whereupon his blood was again drawn and analyzed with the following results:
5,500,000 red blood cells
16.4 grams hemoglobin
50% hematocrit
unknown - blood platelets
10,000 white blood cells which had 3200 lymphocytes. Again, the patient showed an increase in white blood cells and lymphocytes between the 27th day and the 37th day (6500 to 10,000 white blood cells and 2665 to 3200 lymphocytes, respectively).

The patient continued taking doses of *Asphodelus tenuifolius* through the 41st day whereupon a blood test taken on the 41st day showed:

4,950,000 red blood cells
14.0 grams hemoglobin
48% hematocrit
unknown - blood platelets
8800 white blood cells which had 3256 lymphocytes. While there was a decrease overall in white blood cells in the patient from the 37th and 41st day test, the lymphocyte count remained basically unchanged (3200 and 3256, respectively).

The patient was given doses of *Asphodelus tenuifolius* from 41st through the 46th day, whereupon blood was drawn for the last time. This last analysis showed:

5,280,000 red blood cells
16.5 grams hemoglobin
50% hematocrit
370,000 blood platelets
12,800 white blood cells with 2176 lymphocytes. The above blood analysis showed that the patient's white blood cell increased but at these levels lymphocyte count dropped.

The above-cited blood tests reveal that generally a patient that undergoes treatment with the *Asphodelus tenuifolius* extract solution will generally have an increase in white blood cell count and the corresponding increase of lymphocytes.

EXAMPLE 6

*Asphodelus tenuifolius* extract was administered to a male subject with a white blood cell count within the normal levels. The purpose was to examine the effects of the extract in the absence of any interfering infectious elements. The subject whose initial white blood cell count was approximately 7500 took the extract for a period of two days (twice daily). On the third day the subject's blood was drawn and analyzed, revealing:

5,300,000 red blood cells
16.2 grams hemoglobin
50% hematocrit
unknown - blood platelets
9,000 white blood cells which had 2,700 lymphocytes. Again the results show an increase in white blood cell count. One month after the administration took place the subject's blood was drawn again revealing:

5,300,000 red blood cells
16.1 grams hemoglobin
50% hematocrit
unknown - blood platelets
7,800 white blood cells which had 2,574 lyphocytes. Evidently, the blood cell count returned to normal. There have been no side effects to date.

It will now be appreciated that the present invention provides a composition and new use therefor that increases the number of white blood cells and correspondingly increases the percentage of lymphocytes.

The foregoing description is for purposes of illustration, rather than limitation of the scope of protection accorded this invention. The latter is to be measured by the following claims, which should be interpreted as broadly as the invention permits.

The invention claimed is:

1. A composition for treating white blood cell deficiency in human beings or animals comprising, as an active pharmaceutical agent, an effective amount of an herb extract, wherein said herb is from the genus Asphodelus, and said active agent is admixed with a pharmaceutically acceptable carrier.

2. The composition of claim 1 wherein said herb is from the species tenuifolius.

3. The composition of claim 1 wherein said carrier is water.

4. The composition of claim 1 comprising:
about 40 grams to about 60 grams by weight of said herb.

5. The composition of claim 4 comprising 50 grams of said herb.

6. The composition of claim 4 wherein the carrier comprises about 1.5 liters to about 2.5 liters by weight of liquid solution.

7. The composition of claim 6 comprising 2 liters of water.

8. The composition of claim 1 wherein said herb extract comprises an aqueous extract of a woody stem, a root system, a plurality of loculicidal capsules and a plurality of seeds.

9. The composition of claim 1 wherein said herb is ingested orally.

10. The composition of claim 1 wherein said herb is Asphodelus tenuifolius and said carrier is water.

11. A method of treating white blood cell deficiency in human beings or animals comprising the step of administering thereto an effective amount of a therapeutically active composition having as an active pharmaceutical an extract of at least one plant of the Asphodelus genus and being admixed with a pharmaceutically acceptable carrier.

12. The process of claim 11 wherein said herb is from the species tenuifolius.

13. The method of claim 11 wherein said carrier is water.

14. The method of claim 11 comprising: about 40 grams to about 60 grams by weight of said extract.

15. The method of claim 14 comprising:
50 grams of said extract.

16. The method of claim 14 wherein the carrier comprises about 1.5 liters to about 2.5 liters by weight of liquid solution.

17. The method of claim 16 wherein the carrier comprises 2 liters of water.

18. The method of claim 11 wherein said extract comprises a woody stem, a root system, a plurality of loculicidal capsules and a plurality of seeds.

19. The method of claim 11 wherein said composition is ingested orally.

20. The method of claim 11 wherein said treatment results in an increase in white blood cells and said increase corresponds to an increase in the percentage of lymphocytes.

21. The method of claim 11 wherein said plant is Asphodelus tenuifolius and said carrier is water.

22. The method of claim 11 wherein said extract is prepared by adding about 40 to about 60 grams of Asphodelus tenuifolius to about 1.5 liters to about 2.5 liters of water, boiling the resulting mixture for about 15 to about 25 minutes and recovering said extract.

* * * * *